United States Patent [19]
Perez

[11] Patent Number: 5,912,266
[45] Date of Patent: Jun. 15, 1999

[54] BETA$_2$ INTEGRIN CELL ADHESION MOLECULE INHIBITORS

[75] Inventor: Mary Shirley Perez, San Diego, Calif.

[73] Assignee: American Home Products Corporation, Madison, N.J.

[21] Appl. No.: 08/910,261

[22] Filed: Aug. 13, 1997

Related U.S. Application Data

[60] Provisional application No. 60/024,417, Aug. 21, 1996.

[51] Int. Cl.⁶ .................................................. A61K 31/35
[52] U.S. Cl. .......................... 514/460; 514/825; 514/826; 514/866; 514/903
[58] Field of Search .............................................. 514/460

[56] References Cited

U.S. PATENT DOCUMENTS

| | | |
|---|---|---|
| 3,909,362 | 9/1975 | Jiu et al. . |
| 5,232,917 | 8/1993 | Bolger et al. . |

OTHER PUBLICATIONS

Marlin et al., Cell, vol. 51, pp. 813–819, 1987.
Rothlein et al J. of Immunology, vol. 137, pp. 1270–1274, 1986.
Makgoba et al Nature, vol. 331, pp. 86–88, 1988.
Dustin et al., J. of Immunology, vol. 137, pp. 245–255, 1986.
Mizuba et al. Can. J. Microbiol., vol. 21, pp. 1781–1787, 1975.
Argoudelis et al., Tetrahedron Letters, vol. 18, pp. 1969–1973, 1966.
Owen et al., Antimicrobial Agents and Chemotherapy, vol. 1965, pp. 804–807, 1966.
Ramesh et al., Tetrahedron: Asymmetry, vol. 1, pp. 137–140, 1990.
Staunton et al., Cell, vol. 52, pp. 925–933, 1988.

*Primary Examiner*—Rebecca Cook
*Attorney, Agent, or Firm*—Steven R. Eck

[57] ABSTRACT

This invention concerns compositions and methods utilizing a compound of the formula:

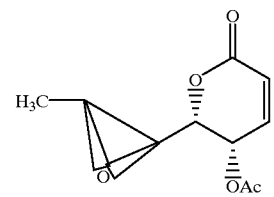

for reducing or controlling inflammation and treating pathological conditions mediated by intercellular adhesion. More particularly, the present invention concerns compositions and methods for blocking or modulating the function of the Beta$_2$ Integrin family of cell adhesion molecules.

7 Claims, No Drawings

BETA₂ INTEGRIN CELL ADHESION MOLECULE INHIBITORS

This application claims the benefit of U.S. provisional application Ser. No. 60/024,417, filed Aug. 21, 1996.

This invention concerns compositions and methods for reducing or controlling inflammation and treating pathological conditions mediated by intercellular adhesion. More particularly, the present invention concerns compositions and methods for blocking or modulating the function of the Beta₂ Integrin family of cell adhesion molecules.

BACKGROUND OF THE INVENTION

Stanley P. Owen and B. K. Bhuyan describe the isolation of the crystalline antibiotic 2H-Pyran-2-one, 6-(1,2-epoxypropyl)-5,6-dihydro-5-hydroxy acetate, which they refer to as U-13,933, in their article "Biological Properties of a New Antibiotic, U-13,933", Antimicrobial Agents and Chemotherapy-1965, copyright 1966, pp. 804–807.

A. D. Argoudelis and J. F. Zieseri described further structural specifications of the antibiotic U-13,933 in "The Structure of U-13,933, A New Antibiotic", Tetrahedron Letters No. 18, pp. 1969–1973, 1966.

U.S. Pat. No. 3,909,362 (Jiu et al.) discloses and claims a process for the production of the antimicrobial agents 5,6-dihydro-5-(S)-acetoxy-6(S)-(1',2'-trans-epoxypropyl)2H-pyran-2-one, 5,6-dihydro-5-(R)-acetoxy-6-(S)-(1',2'-trans-epoxypropyl)2H-pyran-2-one, and 5,6-dihydro-5(S)-acetoxy-6-(S)-(1',2'-trans-propenyl)2H-pyran-2-one comprising growing Aspergillus sp. NRRL 5769 or Aspergillus sp. NRRL 5770 in an aqueous nutrient medium containing sitosterol or sitostenone and isolating the compounds from the medium.

The three metabolites taught in the Jiu et al. patent, above, were further explained as showing antimicrobial activity against *C. albicans,* and against specific bacteria, fungi and a trichomonad by S. Mizuba et al. in "Three antimicrobial metabolites from *Aspergillus caespitosus*", Can. J. Microbiol., Vol. 21, 1975, pp. 1781–1787.

In their article "Total Synthesis of (+)-Asperlin", Tetrahedron:Assymetry Vol. 1, No. 3. pp. 137–140, 1990, Subban Ramesh and Richard W. Franck describe a stereochemically unambiguous synthesis of (+)-asperlin, a crystalline antibiotic from *Aspergillus nidulans,* from L-rhamnose and cite the configuration of the antibiotic as 4S, 5S, 6S, 7R.

BRIEF DESCRIPTION OF THE INVENTION

The present invention comprises compositions and methods for blocking or modulating the function of the Beta₂ Integrin family of cell adhesion molecules in a mammal, preferably in a human, the compositions and methods utilizing the compound having the structure:

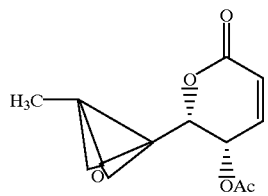

which is named 6,7-Anhydro-2,3,8-trideoxy-D-galacto-oct-2-enoic acid.delta.-lactone 4-acetate, also referred to as 5,6-dihydro-5(S)-acetoxy-6(S)-(1,2-trans-epoxypropyl)-2H-pyran-2-on.

DETAILED DESCRIPTION OF THE INVENTION

The present invention includes pharmaceutical compositions and methods of administering to a mammal, preferably to a human, the compound of this invention to inhibit intercellular adhesion mediated by the $\beta_2$ Integrin family of cell surface molecules. Through this inhibitory activity the pharmaceutical compositions and methods of the present invention are useful in treating or inhibiting inflammatory and other pathological responses associated with cell adhesion. Moreover, the methods of the present invention are useful in treating or inhibiting the pathological conditions where leukocytes and lymphocytes cause cellular or tissue damage.

Through this inhibitory action, the present invention includes methods comprising administering to a mammal in need thereof a therapeutically effective amount of the compound of the present invention to treat the conditions including, but not limited to, asthma, stroke, reperfusion injury, trauma, transplantation rejection, and atherosclerosis. The methods of this invention also include the treatment of autoimmune diseases including, but not limited to arthritis, lupus, multiple sclerosis, Type I diabetes, psoriasis, inflammatory bowel disease, and other inflammatory diseases and conditions.

This invention also comprises pharmaceutical compositions utilizing the compound of this invention. The compound of the present invention may be administered in any manner sufficient to deliver a therapeutic dose, including orally, parenterally or topically. Oral formulations will likely be preferred for most chronic ailments, with parenteral administrations being particularly useful for acute maladies, such as trauma or stroke. Topical formulations may be more desirable for certain autoimmune problems, such as psoriasis. These compounds may be administered neat or with a pharmaceutical carrier to a mammal in need thereof. The pharmaceutical carrier may be solid or liquid.

A solid carrier can include one or more substances which may also act as excipients, flavoring agents, lubricants, solubilizers, suspending or stabilizing agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars such as sucrose, glucose, fructose and confectioner's sugar, lactose, dextrin, dry starch (e.g. corn, potato or tapioca starch), gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredients can be dissolved or suspended in a pharmaceutically acceptable liquid carrier such as water, an organic solvent, a mixture of both, or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably a sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

Preferably, the pharmaceutical composition is in unit dosage form, e.g. as tablets or capsules. In such form, the composition is subdivided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. The dosage to be used in the treatment must be subjectively determined by the attending physician.

The dosage requirements will vary with the particular pharmaceutical composition employed, the route of administration, the severity of the symptoms presented and the particular subject being treated. Projected daily dosages of active compound would be from about 0.1 $\mu$g/kg to about 100 mg/kg, preferably between 0.001–25 mg/kg, and more preferably between 0.01–5 mg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based upon experience with the individual subject treated. Preferably, the pharmaceutical composition is in unit dosage form, e.g. as tablets or capsules. In such form, the composition is sub-divided in unit dose(s) containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

In addition, the compounds of this invention may be employed as a solution, cream, or lotion by formulation with pharmaceutically acceptable vehicles containing 0.5–5 percent, preferably about 2%, of active compound which may be administered to an affected area, such a surface area exhibiting the effects of psoriasis.

The following examples demonstrate the ability of the compounds of this invention to selectively inhibit, block or modulating the function of the Beta$_2$ Integrin family of cell adhesion molecules. The specific compound referred to as asperlin in the Examples below is 6,7-Anhydro-2,3,8-trideoxy-D-galacto-oct-2-enoic acid.delta.-lactone 4-acetate, also referred to herein as 5,6-dihydro-5(S)-acetoxy-6(S)-(1,2-trans-epoxypropyl)-2H-pyran-2-one.

EXAMPLE I

Asperlin inhibits the adhesion of activated, $\beta_2$ integrin-expressing HL60 cells to recombinant soluble ICAM-1

Materials

HL60 cells were provided by the American Type Culture Collection (ATCC No. CCL240) and were used between passages 20 to 30 as the control $\beta_2$ integrin expressing cells, following stimulation for exactly four days in culture media containing dimethylsulfoxide (DMSO). Culture media was comprised of RPMI 1640 (Gibco No. 3201870AJ) supplemented with Penicillin (100 Units/ml)/Streptomycin Sulfate (100 mg/ml) (Gibco No. 600-5145AE), L-Glutamine (2 mM) (Gibco No. 320-5030PG), and 10% heat inactivated fetal bovine serum (FBS, Hyclone No. A-1111L). Fetal bovine serum was heat inactivated by incubating in a 56° C. water bath for 30 minutes. Stimulation of the expression of the $\beta_2$ integrin on HL60 cells was achieved by growing the cells at a density of $2.5 \times 10^5$ cells per ml of culture media for four days in the presence of 1.25% DMSO. Following the removal of the DMSO containing media, the $\beta_2$ integrin on these cells was activated to a high affinity ICAM-1 binding state by the addition of 0.1 nM of (PMA) and PMN Buffer. This buffer was comprised of Hank's balanced salt solution (HBSS) supplemented with 1.2 mM calcium chloride, 1 mM magnesium chloride, 2% glucose, 20 $\mu$M HEPES buffer. The ICAM-1 used to measure the adhesion of $\beta_2$ integrin-bearing cells was obtained from cloning and expression of recombinant, soluble, human ICAM-1 using a baculovirus expression system and standard molecular biology technology. Soluble ICAM-1 was cloned by cleaving ICAM-1 DNA, purchased from R & D Systems, with restriction enzymes to obtain DNA that codes for the soluble (non-membrane) form of the protein. This DNA was then cloned into a baculovirus vector and the expression of soluble ICAM-1 was achieved in Sf9 cells using a kit obtained from Invitrogen Corporation. The soluble ICAM-1 was purified by passing the media from the ICAM-1 expressing cells over an anti-ICAM-1 antibody-linked sepharose column prepared using a standard immunoaffinity chromatography kit obtained from Pierce Inc.

Procedure 200 ng of purified, recombinant, soluble ICAM-1 contained in 100 $\mu$l of PBS was added to wells of a flat bottom, 96 well EIA/RIA plate (Corning No. 25801), covered with an adhesive backed plate sealer (Linbro No. 76-401-05) and incubated for at least 18 hours at 4° C. to allow ICAM-1 to bind to the assay wells, prior to the addition of the $\beta_2$ integrin expressing HL60 cells.

HL60 cells were grown in 1.25% DMSO for 4 days and pelleted by centrifugation in a Sorvall RT6000 tabletop centrifuge for 5 minutes, 1000 rotations per minute (rpm), at room temperature. The resulting HL60 cell pellet was resuspended in 50 ml sterile Dulbecco's phosphate buffered saline (dPBS) (Gibco No. 310-4040AJ). The resulting cell pellet was resuspended in 50 ml dPBS and the cell concentration was determined using a hemacytometer. The cells were pelleted as described above and resuspended in PMN Buffer to 15 to $20 \times 10^6$ cells/ml. The resuspended HL60 cells were fluorescently labeled by mixing the cells with an equal volume of a 25 $\mu$M solution of Calcein AM (Molecular Probes No. C-1430) dye that had been dissolved in PMN Buffer. HL60 cells in the calcein AM solution was incubated in a 37° C. waterbath for 10 minutes with intermittent swirling of the reaction tube. The labeling reaction was stopped by the addition of 13 ml of ice-cold PMN Buffer and the cells were pelleted by centrifugation at 2000 rpm for 5 minutes at 4° C.

The labeled cell pellet was resuspended in 15 ml of ice-cold PMN Buffer and the cell density was determined using a hemacytometer. Cells were then pelleted by centrifugation at 2000 rpm for 5 minutes followed by resuspension in ice-cold PMN Buffer to $2 \times 10^5$ cells/40 μl. The labeled cell suspension was placed in the dark at room temperature while asperlin containing solutions were prepared.

Asperlin was solubilized in 100% DMSO at a concentration of 50 mg/ml. This stock was then diluted to 400 μg/ml with PMN Buffer and serial dilutions of the 400 μg/ml asperlin solution were prepared using PMN buffer containing 2% DMSO to obtain solutions ranging from 200 μg/ml to 1.56 μg/ml.

The ICAM-1 assay plate was removed from 4° C. and allowed to warm to room temperature and non-adherent ICAM-1 was aspirated from the assay plate using a multichannel pipettor. 200 μl of 1% Tween-20 in dPBS was added to the ICAM-1 coated assay wells and the plate was incubated for exactly 2 minutes at room temperature. The 1% Tween-20/dPBS solution was removed from the wells by inverting the assay plate and shaking out the liquid. Wells of the assay plate were washed 4× with 200 μl/well of PMN Buffer. After each wash, the plate was inverted and blotted on paper toweling to remove excess liquid. 50 μl of the serially diluted asperlin was added to wells of the assay plate. The control wells received 50 μl of PMN buffer containing 2% DMSO and the assay plate was incubated at room temperature for 10 minutes.

Calcein labeled cells, that had been gently mixed by swirling, were added to the wells in 40 μl volumes equal to $2 \times 10^5$ cells/well, followed immediately by addition of 10 μl of $1 \times 10^{-6}$ M PMA solution to all assay wells using a multichannel pipettor. The well contents were mixed using the same multichannel pipettor and the assay plate was incubated for 30 minutes in a 37° C., 5% $CO_2$, humidified incubator.

The assay plate was removed from the 37° C. incubator and total fluorescence of the labeled $\beta_2$ integrin expressing cells in each well of the assay plate was measured using a fluorescent microtiter plate reader (Cytofluor, Millipore Corp). Non-adherent cells were aspirated from the wells of the assay plate using a multichannel pipettor. Wells of the assay plate were washed 3× with 200 μl PMN buffer/well. 100 μl of PMN buffer was added to wells of the assay plate. The fluorescence of the adherent, activated, $\beta_2$ integrin expressing cells was measured using the fluorescent plate reader, as just described.

The percentage of $\beta_2$ integrin expressing cells adhering to ICAM-1 wells was quantitated by the following equation:

% Cells Bound=(Bound Cell Fluorescence÷Total Cell Fluorescence)×100

The percentage of inhibition of $\beta_2$ integrin expressing cells adhering to ICAM-1 in the presence of asperlin was quantitated by the equation: % Inhibition of Cell Adhesion= 100%−[(Average % Cells Bound in the presence of asperlin÷Average % Cells Bound in control wells)×100]

The results obtained in this experiment, shown in the following table (Table I), demonstrated that asperlin blocks the adhesion of activated $\beta_2$ integrin expressing cells to ICAM-1. The control wells, that do not contain asperlin, represent 0% inhibition in binding of $\beta_2$ integrin expressing cells to ICAM-1. This suggests that asperlin is an inhibitor of $\beta_2$ integrin mediated adhesion to ICAM-1.

TABLE I

| Asperlin μg/ml | Total Cell Fluorescence (fluorescence units/well) | Bound Cell Fluorescence (fluorescence units/well) | Percent Cells Bound | Average Percent Cells Bound | % Inhibition of Cell Adhesion |
|---|---|---|---|---|---|
| 200 | 5764 | 29 | 0.5 | 0.5 | 98 |
|  | 5796 | 28 | 0.5 |  |  |
| 100 | 6504 | 45 | 0.7 | 0.6 | 97.5 |
|  | 6377 | 31 | 0.5 |  |  |
| 50 | 5764 | 82 | 1.4 | 1.4 | 94 |
|  | 5829 | 77 | 1.3 |  |  |
| 25 | 6522 | 171 | 2.6 | 4 | 83 |
|  | 6080 | 320 | 5.3 |  |  |
| 12.5 | 6029 | 589 | 10 | 12 | 50 |
|  | 6829 | 768 | 13 |  |  |
| 6.25 | 6541 | 1003 | 15 | 17 | 29 |
|  | 6218 | 1161 | 19 |  |  |
| 3.125 | 5747 | 1862 | 32 | 33 | −36 |
|  | 6166 | 2077 | 34 |  |  |
| 1.56 | 6236 | 1551 | 25 | 26 | −8 |
|  | 6468 | 1755 | 27 |  |  |
| 0, Control | 5961 | 1231 | 21 | 24 |  |
|  | 5796 | 1433 | 25 |  |  |
|  | 5651 | 1129 | 20 |  |  |
|  | 6149 | 1750 | 28 |  |  |
|  | 6063 | 1740 | 29 |  |  |
|  | 5731 | 1073 | 19 |  |  |

EXAMPLE II

Asperlin does not inhibit the adhesion of activated, $\beta_1$ Integrin-expressing U937 cells to human fibronectin Materials U937 cells, a human monocyte-like, histiocytic lymphoma cell line, was acquired from American Type Culture Collection (ATCC No. CRL-1593). The cells were grown in the culture media described in Example I, materials. Cells were subcultured when the cell density was approximately $1 \times 10^6$ cells per ml. The $\beta_1$ integrins on U937 cells were activated to bind to fibronectin by the addition of PMN Buffer, described in Example I. The human fibronectin (Gibco, No. XOO1) was diluted to 3.5 μg/ml with dPBS. A 1% Bovine Serum Albumin (BSA; Fraction V, ICN Corp., No. 810032) solution was prepared in dPBS and was sterile filtered using a 0.22 mM disposable filter apparatus (Corning No. 25932-200) before use. The 1% BSA solution was used for blocking non-specific binding sites on the plastic wells of the assay plate. The assay plates used were Corning 96-well EIA/RIA plates (No. 25801).

Procedure 350 ng of human fibronectin contained in 100 μl of dPBS was added to wells of the assay plate. The control wells were filled with dPBS only. The assay plate was incubated at room temperature for exactly two hours to allow the fibronectin to bind to the assay wells. The fibronectin solution was aspirated from the wells of the assay plate and the wells were washed 3× with 200 μl/well of dPBS. The assay wells were filled with the 1% BSA solution. Additional wells, not coated with fibronectin, were also filled with the 1% BSA solution; these wells were used to measure non-specific cell adherence to the plastic assay plate. The assay plate was incubated for 30 minutes at room temperature. The 1% BSA solution was removed from the wells of the assay plate by aspiration using a multichannel pipettor. The assay wells were washed 3× with 200 μl/well of dPBS. Approximately 50 μl of dPBS was added to the assay wells to ensure that they would not dry out prior to the initiation of the assay.

U937 cells were harvested from culture, washed and labeled with calcein AM fluorescent dye as outlined in Example I, except that the concentration of calcein used to label U937 cells was 12.5 µM and cells were sedimented by centrifugation at 1000 rpm for 5 minutes. After the final wash (see Example I), the U937 cells were resuspended in ice-cold PMN Buffer to $1.25 \times 10^5$ cells/40 µl. The cell suspension was placed in the dark at room temperature until needed. The asperlin solutions were prepared as described in Example I.

The 50 µl of dPBS remaining in the wells of the assay plate was removed by inverting the assay plate and tapping on paper toweling. 50 µl of the serially diluted asperlin solution was added to wells of the assay plate. Control wells received PMN buffer containing 2% DMSO and the assay plate was incubated for 10 minutes at room temperature.

Calcein labeled cells, that had been gently mixed by swirling, were added to the wells in 40 µl volumes equal to $1.25 \times 10^5$ cells/well and 10 µl of PMA solution was immediately added to the wells of the assay plate and the assay was continued as described in Example 1. 100 µl of PMN buffer was added to all wells of the assay plate. The fluorescence of the adherent, activated $\beta_1$ integrin expressing cells was measured using a fluorescent plate reader, as described in Example I.

The percentage of $\beta_1$ integrin expressing cells adhering to fibronectin coated wells was quantitated by the equation: % Cells Bound=((Bound Cell Fluorescence−Average Bound Fluorescence of the Non-specific Binding Control)÷Total Cell Fluorescence)×100.

The percentage of inhibition of $\beta_1$ integrin expressing cell adhesion to human fibronectin in the presence of asperlin was quantitated, as described in Example I. The results obtained in this experiment, shown in the following table (Table II), demonstrate that asperlin does not block the adhesion of $\beta_1$ integrin expressing cells to fibronectin.

TABLE II

| Asperlin µg/ml | Total Cell Fluorescence (fluorescence units/well) | Bound Cell Fluorescence (fluorescence units/well) | Percent Cells Bound | Average Percent Bound | % Inhibition Cell Adhesion |
|---|---|---|---|---|---|
| 200 | 3019 | 2222 | 61 | 67 | 3 |
|  | 3475 | 2736 | 68 |  |  |
|  | 3455 | 2846 | 71 |  |  |
| 100 | 3407 | 2466 | 61 | 69 | 0 |
|  | 3534 | 2854 | 70 |  |  |
|  | 3738 | 3194 | 75 |  |  |
| 50 | 2960 | 2391 | 68 | 73 | −6 |
|  | 3257 | 2791 | 74 |  |  |
|  | 3635 | 3203 | 77 |  |  |
| 25 | 3276 | 2404 | 61 | 69 | 0 |
|  | 3485 | 2870 | 71 |  |  |
|  | 3455 | 2969 | 75 |  |  |
| 12.5 | 3045 | 2331 | 64 | 70 | −1 |
|  | 3248 | 2683 | 71 |  |  |
|  | 3495 | 2985 | 74 |  |  |
| 6.25 | 3194 | 2292 | 60 | 62 | 10 |
|  | 3248 | 2344 | 60 |  |  |
|  | 3294 | 2529 | 65 |  |  |
| 3.125 | 3594 | 3132 | 76 | 75 | −9 |
|  | 3686 | 3140 | 75 |  |  |
|  | 3446 | 2895 | 73 |  |  |
| 1.56 | 3465 | 3002 | 75 | 75 | −9 |
|  | 3645 | 3140 | 76 |  |  |
|  | 3697 | 3132 | 74 |  |  |
| 0, Control | 2696 | 2344 | 66 | 69 |  |
|  | 2919 | 2318 | 66 |  |  |
|  | 3105 | 2384 | 64 |  |  |
|  | 3436 | 2846 | 72 |  |  |
|  | 3379 | 2799 | 71 |  |  |
|  | 3322 | 2646 | 68 |  |  |
|  | 3717 | 3221 | 76 |  |  |

TABLE II-continued

| Asperlin µg/ml | Total Cell Fluorescence (fluorescence units/well) | Bound Cell Fluorescence (fluorescence units/well) | Percent Cells Bound | Average Percent Bound | % Inhibition Cell Adhesion |
|---|---|---|---|---|---|
|  | 3455 | 2838 | 71 |  |  |
|  | 3294 | 2572 | 66 |  |  |
| Non-Specific Binding | 3584 | 378 |  |  |  |
|  | 3370 | 328 |  |  |  |
|  | 3350 | 339 |  |  |  |
|  | 3341 | 409 |  |  |  |
|  | 3239 | 405 |  |  |  |
|  | 2744 | 461 |  |  |  |

EXAMPLE III

Asperlin does not inhibit the adhesion of HL60 Cells to E-selection

The following experiments demonstrate that asperlin does not affect the binding of HL-60 cells to recombinant, soluble, human E-selectin (rsE-selectin).

Materials rsE-selectin was prepared and purified using standard molecular biology techniques. HL60 cells were obtained from American Type Culture Collection (ATCC) and maintained in culture media, as described in Example I, except that cells could be used in the assay at any passage number. Other materials required for the assay are as described in Examples I and II.

Procedure 200 ng of purified, recombinant, soluble E-selectin contained in 100 µl of dPBS was added to wells of a flat bottom 96 well EIA/RIA plate. The control wells were filled with dPBS only and the assay plate was incubated at 4° C. for at least 18 hours to allow the rsE-selectin to bind to assay wells. The rsE-selectin solution was removed from the wells of the assay plate, washed, and blocked with 1% BSA, as described in Example II.

HL60 cells were harvested from culture, washed and labeled with calcein AM as outlined in Example I, except that the concentration of calcein used to label the HL-60 cells was 12.5 µM and cells were centrifuged at 1000 rpm for 5 minutes. After the final cell wash (see Example I), the cells were resuspended in ice-cold PMN buffer to $1.0 \times 10^5$ cells/ 40 µl and the cells were placed in the dark at room temperature until added to the assay plate.

The asperlin solutions were prepared as described in Example I. The dPBS remaining in the wells of the assay plate was removed by inverting the plate and tapping it on paper toweling and the assay was performed as described in Example II. 100 µl of PMN buffer was added to all wells of the assay plate and the fluorescence of the adherent HL-60 cells binding to rsE-selectin was measured using a fluorescent plate reader, described in Example I. The percentage of HL60 cells binding to E-selectin and the percentage of inhibition of HL60 cell adhesion to E-selectin in the presence of asperlin were also quantitated as described in Example II.

The results obtained in this experiment, shown in the following table (Table III), indicate that asperlin does not inhibit E-selectin mediated HL60 cell binding.

TABLE III

| Asperlin μg/ml | Total Cell Fluorescence (fluorescence units/well) | Bound Cell Fluorescence (fluorescence units/well) | Percent Cells Bound | Average Percent Bound | % Inhibition |
|---|---|---|---|---|---|
| 200 | 1720 | 1124 | 52 | 48 | 8 |
|  | 1478 | 887 | 44 |  |  |
| 100 | 1832 | 1412 | 64 | 62 | −19 |
|  | 1457 | 1096 | 59 |  |  |
| 0, Control | 1526 | 977 | 49 | 52 |  |
|  | 1544 | 1017 | 51 |  |  |
|  | 1474 | 953 | 50 |  |  |
|  | 1559 | 1118 | 57 |  |  |
|  | 1554 | 1105 | 56 |  |  |
|  | 1637 | 1084 | 52 |  |  |
| Non-specific Binding | 1520 | 128 |  |  |  |
|  | 1375 | 89 |  |  |  |
|  | 1351 | 199 |  |  |  |
|  | 1650 | 225 |  |  |  |
|  | 1647 | 270 |  |  |  |
|  | 1760 | 479 |  |  |  |

EXAMPLE IV

MTT Cytotoxicity Assay

This experiment describes the affect of asperlin on cellular respiration (mitochondrial activity) by measuring the reduction of the tetrazolium salt MTT to formazan crystals (Moseman, et al). This assay served as a control to ensure that the decrease in the fluorescence observed in Example I, Table I, was not the result of the fluorescent dye leaking from the cells due to disruption of the cell membrane. To address this issue, the mitochondrial activity of $\beta_2$ and $\beta_1$ integrin expressing cells in the presence of asperlin was quantitated using a commercially available MTT cytotoxicity kit (Promega No. G4100).

Materials

HL60 and U937 cells were purchased from the American Type Culture Collection (ATCC) and maintained in RPMI 1640 culture media containing 10% heat inactivated fetal bovine serum (refer to Example I, materials). HL60 cells were used between passages 20 and 30. HL60 cells were stimulated by a four day exposure to DMSO, as described in Example I, materials. Falcon round bottom tissue culture plates (No. 3077) were used for the experiment. All remaining reagents were supplied in Promega's MTT cytotoxicity kit (Catalog No. G4100).

Procedure

The assay procedure described in the Promega MTT kit was used with the following changes.

Asperlin was solubilized in 100% DMSO at a concentration of 50 mg/ml. The 50 mg/ml asperlin stock was diluted to 400 μg/ml with culture media containing 5% fetal bovine serum (FBS). This solution was further diluted to 80 and 20 μg/ml with culture media supplemented with 5% FBS plus 2% DMSO. 50 μl of the 20 and 80 μg/ml asperlin solutions were added to wells of a sterile, round bottom 96 well assay plate. Control wells received 50 μl of culture media containing 5% FBS plus 2% DMSO. Duplicate assay wells were prepared such that U937 and HL60 cells could be evaluated on the same plate. The cell density of $\beta_1$ integrin expressing U937, and $\beta_2$ integrin expressing HL60 cell cultures were determined using a hemacytometer.

Cells were harvested by centrifuging for 5 minutes at 1000 rpm, room temperature, in a Sorvall RT600 bench-top centrifuge. The HL60 cell pellet was resuspended in fresh culture media at a concentration of $5 \times 10^6$ cells/ml. The U937 cell pellet was resuspended in fresh culture media at a concentration of $2.5 \times 10^6$ cells/ml. $2.5 \times 10^5$ $\beta_2$ integrin expressing HL60 cells, contained in 50 μl, were added to wells of the assay plate using a multichannel pipettor. In duplicate assay wells, $1.25 \times 10^5$ $\beta_1$ integrin expressing U937 cells, contained in 50 μl, were added to wells of the assay plate using a multichannel pipettor. Assay plates were incubated for either 30 minutes, 60 minutes, or 4 hours in a 37° C. 5% $CO_2$, humidified incubator.

At the appropriate time point, 15 μl of MTT reagent, supplied in the Promega assay kit, was added to each well using a multichannel pipettor. Assay plates were incubated in the 37° C. incubator, as just described, for two hours. The MTT reduction reaction was quenched, and the visible formazan crystals were solubilized by adding exactly 100 μl of Promega's solubilization buffer to each well. Assay plates were incubated for at least 18 hours in the same 37° C. incubator just described to solubilize the formazan reagent. Assay plates were removed from the incubator and allowed to cool to room temperature. The optical density (OD) of each well of the assay plate was determined using a microtiter plate reader (Flow Labs) set at a wavelength of 580 nm with a correction wavelength of 630 nm.

Replicate sample ODs were average. The percentage of inhibition of cellular respiration (mitochondrial activity) by asperlin was quantitated by the following equation:

% Inhibition=(1−(Sample OD÷Average Control OD))×100

The results obtained in this experiment, shown in the following table (Table V), show that asperlin is not cytotoxic to either $\beta_2$ or $\beta_1$ integrin expressing cells and, the reduction in $\beta_2$ integrin mediated cell adhesion by asperlin is not the result of an effect of asperlin on HL60 cellular function.

TABLE V

| Asperlin μg/mL | Cell Type | Time Point | Optical Density | Average Optical Density | % Inhibition MTT Reduction |
|---|---|---|---|---|---|
| 40 | HL60 | 30 min. | .650 | .649 | 27 |
|  |  |  | .646 |  |  |
|  |  |  | .650 |  |  |
| 10 | HL60 | 30 min. | .819 | .819 | 8 |
|  |  |  | .823 |  |  |
|  |  |  | .815 |  |  |
| 0, Control | HL60 | 30 min. | .942 | .895 |  |
|  |  |  | .889 |  |  |
|  |  |  | .891 |  |  |
|  |  |  | .897 |  |  |
|  |  |  | .875 |  |  |
|  |  |  | .873 |  |  |
| 40 | U937 | 30 min. | 1.362 | 1.386 | 11 |
|  |  |  | 1.352 |  |  |
|  |  |  | 1.391 |  |  |
| 10 | U937 | 30 min. | 1.410 | 1.532 | 0 |
|  |  |  | 1.601 |  |  |
|  |  |  | 1.584 |  |  |
| 0, Control | U937 | 30 min. | 1.525 | 1.534 |  |
|  |  |  | 1.551 |  |  |
|  |  |  | 1.509 |  |  |
|  |  |  | 1.484 |  |  |
|  |  |  | 1.550 |  |  |
|  |  |  | 1.582 |  |  |

EXAMPLE V

Asperlin inhibits $\beta_2$ integrin/ICAM-1 homotypic binding

The following experiment describes the inhibition of homotypic (cell:cell) binding of $\beta_2$ and ICAM-1 expressing cells by asperlin. 8866 cells, a human B-cell line, were supplied by Athena Neurosciences (San Francisco, Calif.). These cells constitutively express both the $\beta_2$ integrin referred to as LFA-1, and ICAM-1 on the cell surface. In culture, 8866 cells spontaneously bind, or clump together, as a result of $\beta_2$ integrin binding to ICAM-1. Cell adhesion blocking monoclonal antibodies against LFA-1 have been shown to completely block the binding of $\beta_2$ integrin to ICAM-1, in the interaction referred to as cell:cell homotypic binding (Rothlein, et al.).

Materials 8866 cells were maintained in RPMI 1640 culture media (refer to Example I) supplemented with 10 $\mu$M HEPES buffer (Gibco No. 15630-080). Cells were subcultured when the cell density was approximately $1 \times 10^6$ cells/ml. The anti-LFA-1 monoclonal antibody IOT16 (AMAC), was included in each experiment as a positive control inhibitor of the homotypic binding of LFA-1 to ICAM-1.

Procedure 8866 cells were harvested by centrifuging 5 minutes, at 1000 rpm, room temperature, in a Sorvall RT6000 centrifuge. The cell pellet was resuspended in culture media and cells were counted using a hemacytometer. Cells were re-sedimented by centrifuging 5 minutes, at 1000 rpm, room temperature, in a Sorvall RT6000 centrifuge. The cell pellet was resuspended in culture media at a concentration of $2 \times 10^6$ cells/ml. $2 \times 10^5$ cells contained in 100 $\mu$l were transferred to each well of a flat bottom, 96 well, tissue culture plate (Falcon No. 3072).

Asperlin was solubilized in 100% DMSO at a concentration of 20 mg/ml, 10 mg/ml, 5 mg/ml, and 2.5 mg/ml. These stocks were diluted with culture media to a concentration of 400 $\mu$g/ml, 200 $\mu$g/ml, 50 $\mu$g/ml, and 25 $\mu$g/ml, respectively. Asperlin was added to wells of the assay plate in volumes of 50 $\mu$l per assay well. 50 $\mu$l of culture media containing 2% DMSO was added to control wells of the assay plate. The monoclonal antibody IOT16 was diluted to 20 $\mu$g/ml using culture media containing 2% DMSO. 50 $\mu$l of the 20 $\mu$g/ml antibody solution was added to positive inhibition control wells on the assay plate. A 200 ng/ml solution of PMA was prepared using culture media, and exactly 50 $\mu$l of this solution was added to wells of the assay plate and the assay plate was incubated in a 37° C. 5% $CO_2$, humidified incubator for two hours. The progression of homotypic binding was monitored by microscopic observations after 1 and 2 hours of incubation.

Inhibition $\beta_2$ integrin dependent homotypic binding to ICAM-1 by asperlin was photographically recorded using a Nikon 35 mm camera attached to a Nikon Diaphot 300 inverted microscope (filter setting NCBII, objective 10x, and light setting of photo). Visual inspection of the assay plate after 1 hour of incubation indicated that the monoclonal antibody IOT16 inhibited 8866 cell homotypic binding 100% (cells were not touching or binding to each other). Asperlin was visually observed to also inhibit cell—cell binding in a dose dependent manner. Visual inspection of the assay plate after 2 hours of incubation indicated that the monoclonal antibody IOT16 completely inhibited (100%) 8866 cell homotypic binding. Asperlin inhibited 8866, $\beta_2$ integrin mediated homotypic binding to ICAM-1 in a dose dependent manner. These results confirm the effects of asperlin as a blocker of $\beta_2$ integrin-mediated homotypic (cell:cell) adhesion.

What is claimed:

1. A method for treating in a mammal a pathological condition in which leukocytes and lymphocytes cause tissue damage, the method comprising administering to a mammal in need thereof a therapeutic dosage of a compound of the formula:

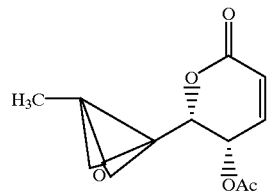

2. The method of claim 1 wherein the mammal is a human.

3. The method of claim 1 wherein the pathological condition is atherosclerosis.

4. The method of claim 1 wherein the pathological condition is transplantation rejection.

5. A method for treating inflammation in a mammal, the method comprising administering to a mammal in need thereof a therapeutic dosage of a compound of the formula:

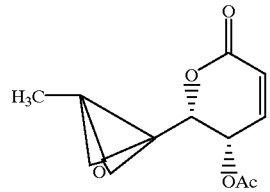

6. A method for inhibition in a mammal pathological responses associated with intercellular adhesion mediated by the $\beta_2$ Integrin family of cell surface molecules, the method comprising administering to a mammal in need thereof a therapeutic dosage of a compound of the formula:

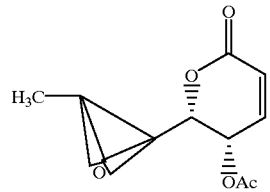

7. The method of claim 6 in which the pathological response associated with intercellular adhesion are asthma, stroke, reperfusion injury, trauma, transplantation rejection, arthritis, lumpus, multiple sclerosis, Type I diabetes, psoriasis, inflammatory bowel disease or atherosclerosis.

* * * * *